United States Patent [19]

Glastra

[11] Patent Number: 5,464,419
[45] Date of Patent: Nov. 7, 1995

[54] EXPANDABLE HOLLOW SLEEVE FOR THE LOCAL SUPPORT AND/OR REINFORCEMENT OF A BODY VESSEL, AND METHOD FOR THE FABRICATION THEREOF

[75] Inventor: Hendrik Glastra, Enschede, Netherlands

[73] Assignee: Industrial Research B.V., Netherlands

[21] Appl. No.: 215,178

[22] Filed: Mar. 21, 1994

[30]    Foreign Application Priority Data

Mar. 22, 1993 [NL] Netherlands ............................. 9300500

[51] Int. Cl.$^6$ .............................. A61M 29/00; A61F 2/04
[52] U.S. Cl. ................................ 606/194; 623/1; 623/12
[58] Field of Search .................... 606/191, 194, 606/195; 623/1, 12, 11; 128/DIG. 8; 604/96, 104

[56]    References Cited

U.S. PATENT DOCUMENTS 4,416,028  11/1983  Eriksson et al. .
4,641,653   2/1987  Rockey .
4,704,207   4/1988  Kreamer .
5,100,429   3/1992  Sinofsky et al. .
5,156,620  10/1992  Pigott .
5,234,456   8/1993  Silvestrini .

FOREIGN PATENT DOCUMENTS 0452219  10/1991  European Pat. Off. .
0521573   1/1993  European Pat. Off. .
2247696   3/1992  United Kingdom .
92/11896  7/1992  WIPO .

*Primary Examiner*—Stephen C. Pellegrino
*Assistant Examiner*—William Lewis
*Attorney, Agent, or Firm*—Ostrolenk, Faber, Gerb & Soffen

[57]    ABSTRACT

The invention provides an expandable double-walled sleeve whose space between the walls is filled with curable material and which is designed for the local support and/or reinforcement of a body vessel, absorbent material being provided between its walls which are fabricated from an essentially non-extensible material. This achieves the advantage that the curable material remains uniformly distributed between the walls of the sleeve even if the sleeve is rolled around a still unexpanded PTA balloon in order to be brought to the desired position by means of said balloon.

15 Claims, 7 Drawing Sheets

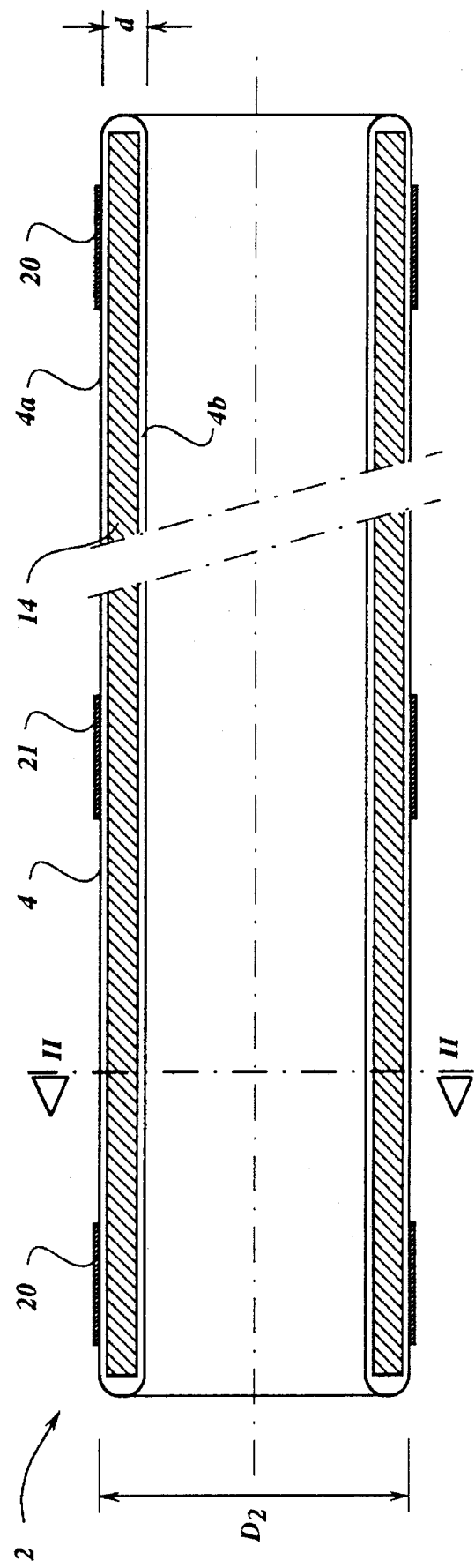
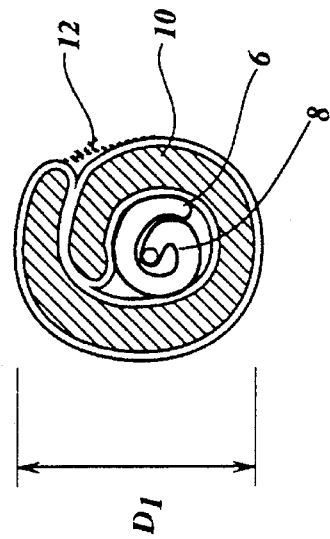
Fig. 3
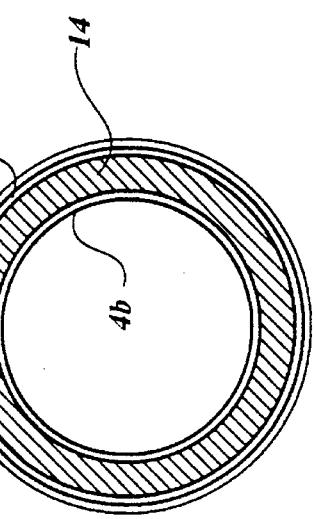
Fig. 2
Fig. 1

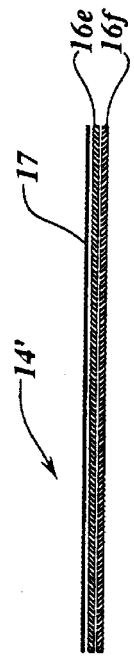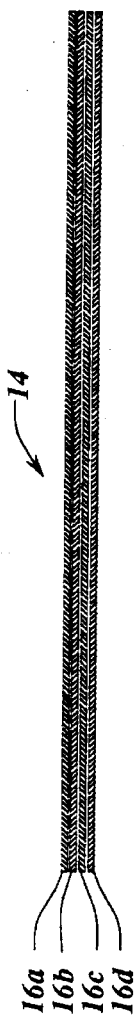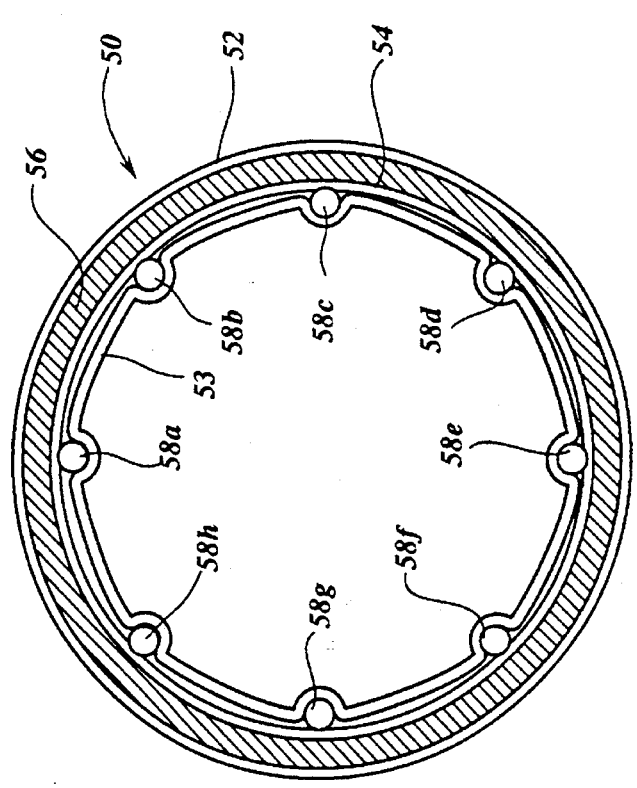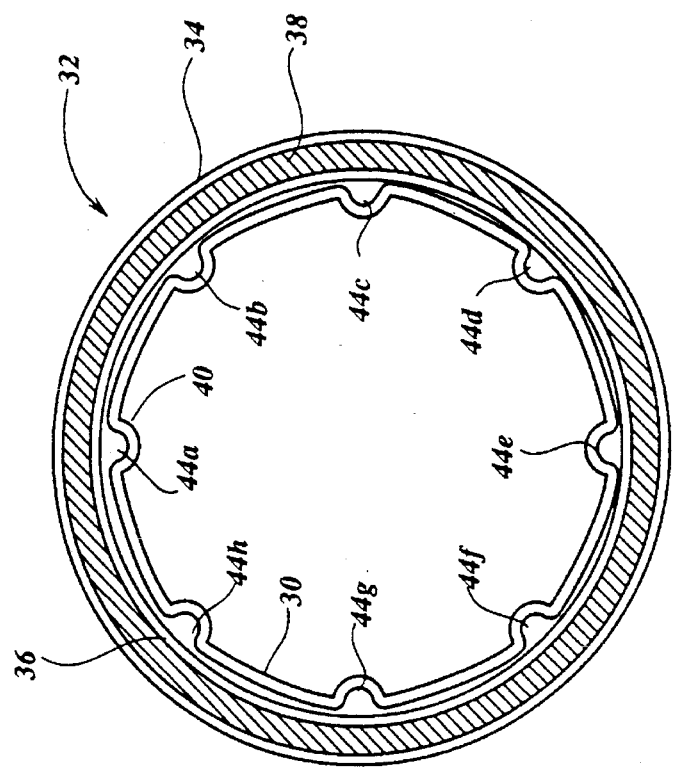
Fig. 4b
Fig. 4a
Fig. 7
Fig. 6

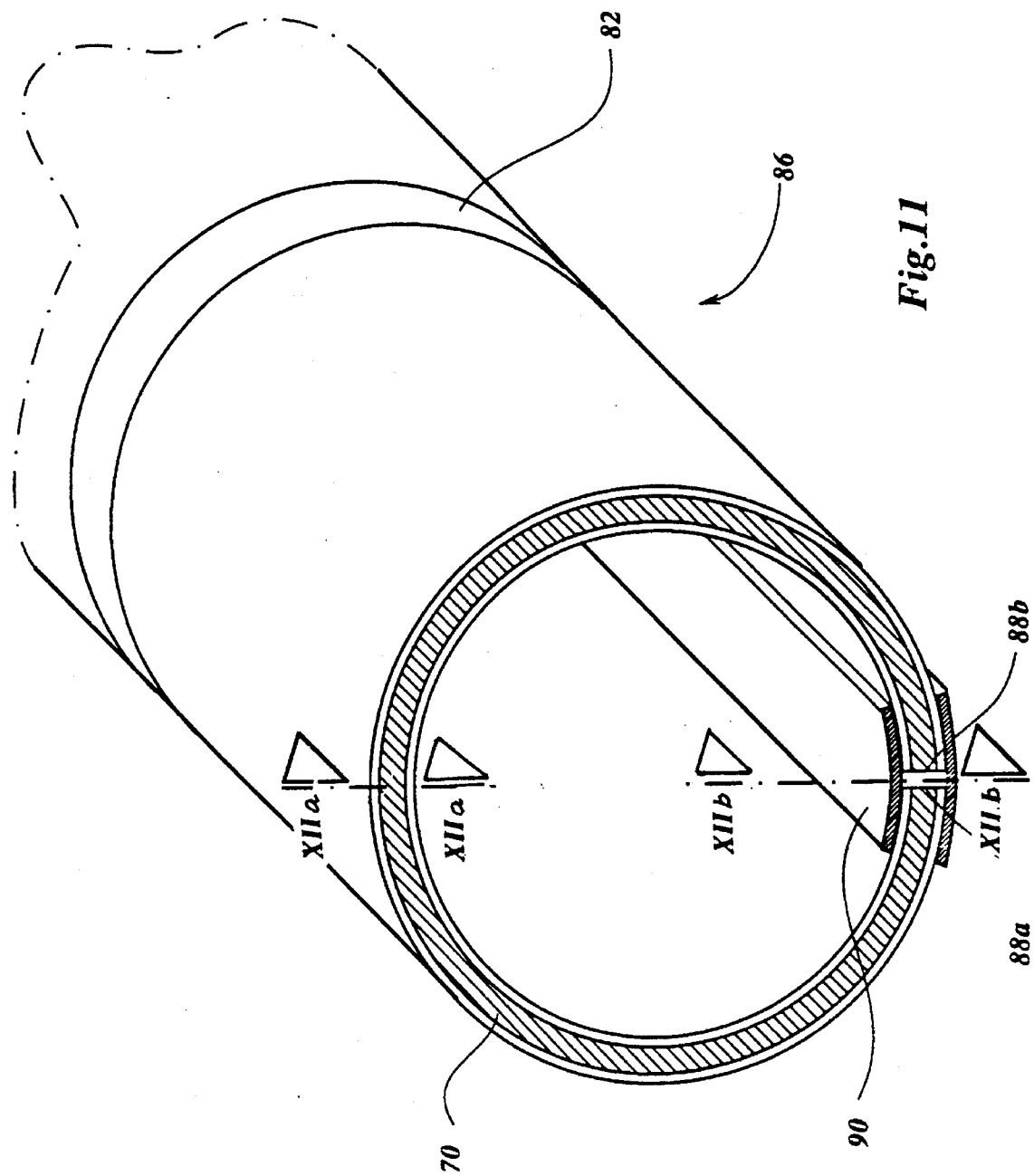

EXPANDABLE HOLLOW SLEEVE FOR THE LOCAL SUPPORT AND/OR REINFORCEMENT OF A BODY VESSEL, AND METHOD FOR THE FABRICATION THEREOF

BACKGROUND OF THE INVENTION

This invention relates to an expandable hollow sleeve in which the space between the walls is filled with curable material and which is designed for the local support and/or reinforcement of a body vessel.

DESCRIPTION OF THE PRIOR ART

Such an expandable sleeve or prosthesis, also referred to as a "stent", is the subject of EP-A-0 452 219. In this publication, a stent is described which is filled from the outside under pressure with a curable synthetic material via a duct introduced with the catheter.

Such a stent cannot be produced in a practically usable form. This is the consequence of the fact that the method of introduction–via a body vessel–imposes limitations on the maximum permitted dimensions: the diameter of the catheter end, together with a PTA balloon and the still unexpanded stent mounted around it, must not exceed, for a patient-friendly treatment, a value of approximately 7 mm and, if used in cardiac surgery, it must not exceed even 2.5 mm. In connection with the above it is observed that "PTA" stands for "Percutaneous Transluminal Angioplasty". According to this, in the meantime wellknown, treatment an inflatable balloon is inserted into a partly blocked artery and thereafter inflating, dilating the artery and removing the restriction. A complete description of this known method is given in Sinofsky (U.S. Pat. No. 5100429), column 1, lines 10–25.

Assuming a still usable thickness of the wall material used of approximately 20 μm, this results, in the most favourable case, in a spacing between the inner and outer wall of the final sleeve of, say, 0.3 mm for a stent which is used for the treatment of, for example, an aneurysm and which must at the same time have an outside diameter of 14–22 mm in the expanded state. Not only can a filling duct which connects thereto not be fabricated, but even if this were to be the case, it is impossible to fill the stent with curable synthetic material via a channel having such a small bore within the time limit set for an intervention and to remove the air escaping during this process via a separate duct. Said air must not end up in the body under any circumstances.

The fact that elastic wall material is used in this known stent makes it impossible to determine the final diameter and shape of the stent with any certainty, which is in fact medically unacceptable. This disadvantageous effect is heightened still further by the fact that the material introduced cannot distribute itself uniformly since the feed duct can be situated only on one side. The stent described is therefore also unusable in practice for the intended purpose, all the more so because there is no guarantee that, when the filling line is broken, which is necessary to withdraw the catheter, no filling material will enter the body.

The intervening European Patent Application 92 201 970.8 in the name of the Applicant, equivalent to U.S. Ser. No. 07/909,051, and EP 0 521 573, has therefore already proposed to fill the sleeve not during the treatment, but at an earlier stage with curable material whose curing process is initiated and accelerated by irradiation with, for example, UV radiation which is supplied via a separate optical fibre and reaches the sleeve via the walls of the PTA balloon and the high-contrast filling fluid.

In a stent of the type described above, it is necessary to ensure that the curable material is distributed uniformly over the entire internal space of said stent after it has expanded. Moreover, in order to be usable in a medically acceptable manner, the final diameter and shape must be capable of being determined beforehand down to tenths of millimeters.

SUMMARY OF THE INVENTION

According to my invention, this is achieved by using absorbent material provided between the non-extensible walls of the sleeve.

The fact that the walls of the sleeve according to the invention consist of non-extensible material offers the great advantage that it has now become possible for the first time to determine the final shape and diameter of the stent down to tenths of millimeters, as a result of which both purely cylindrical shapes and any desired shapes required by a physician are possible, in other words: the stent according to the invention has in fact become a made-to-measure product.

The absorbent material, of which the cells present therein are filled with the curable material, ensures not only a completely uniform distribution of the latter over the entire internal space of the expandable sleeve but, in addition, it gives said sleeve an additional strength in the expanded state, as a result of which the stent having the very thin wall has much greater resistance to the forces exerted thereon.

The absorbent material may be mesh-like, for example it may have the form of a fabric of which one or more individual layers are present. This achieves the effect that the cured synthetic-material filling retains a certain flexibility, which is an advantage for many medical applications.

As curable material, an acrylate known per se may be used. If a single-layer fabric having relatively thick threads is used in this case, a "hand grenade" effect is obtained, which resides in the fact that the cohesive layer of synthetic material present between the inner and outer walls of the sleeve disintegrates into fragments when a radial outward pressure is exerted on the inner wall of the stent. This effect offers hitherto unknown possibilities, since it now becomes possible for the first time to remove a positioned stent nonoperatively, that is to say by means of a catheter. To do this, it is necessary to introduce only a PTA balloon provided with a suitable curable glue on the outside into the stent positioned in the body vessel, to expand the PTA balloon, as a result of which the synthetic-material filling of the stent disintegrates, and to wait until the glue has cured; if the PTA balloon is then allowed to deflate, it shrinks with the stent bonded to it to such a smaller diameter that the whole assembly can be withdrawn from the body vessel.

In order to be able to locate the stent easily or to be able to follow it during its introduction, an identifying mark composed of material which enhances X-ray contrast is preferably provided on it. This contrast-enhancing material may be combined with the absorbent material and, if said contrast-enhancing material is provided on the outside of the latter and is also opaque to UV radiation, it protects the curable material against undesirable radiation incident from the outside. This material may optionally be provided in the form of a strip extending in the circumferential direction.

The presence of the absorbent material has the result that, even if the forces directed radially outwards and exerted on the inner wall are not uniformly distributed during the unfolding, the curable material nevertheless remains uniformly distributed. This makes it possible to make use of a PTA balloon assembly whose outer wall is provided with preformed duct-like or groove-like profilings extending in the longitudinal direction of the balloon, or on whose outer wall one or more ducts are provided which extend in the longitudinal direction of the balloon. This ensures that, during the positioning of the stent, the body vessel concerned is not completely blocked, which is a great advantage in many cases.

The invention moreover provides a method for fabricating an expandable sleeve of the type described above.

Such a method comprises the steps of:

impregnating a strip of absorbent material having a predetermined width ($b_1$) with a suitable curable material, positioning said strip of absorbent material on a strip of film material having a width ($b_2$) essentially equal to twice the width of the strip of absorbent material plus twice the thickness of the absorbent material, folding the longitudinal edges of the film material around the absorbent material, bonding together the end edges of the film material which are laid against one another, preparing a certain length ($l_2$) of the assembly obtained in this way to form a first semi-finished product, bending said semi-finished product over on itself along a line perpendicular to its longitudinal direction until its end edges essentially lie against one another so as to form a second semifinished product, attaching said end edges to one another so as to form a seal.

Preferably the strip of absorbent material is made up of a plurality of layers, while the absorbent material can be combined with material which enhances X-ray contrast.

The attachment of the end edges of the film material to one another is preferably implemented by means of an adhesive tape, for instance using an adhesive tape which is also provided with a layer of material which enhances X-ray contrast.

The tape can be provided with a layer of woundadhesive, and can be present at a plurality of positions on the sleeve.

Finally the attachment of the end edges of the first semifinished product to one another, to obtain the second semifinished product, is preferably carried out by means of an adhesive tape.

SUMMARY OF THE DRAWINGS

FIG. 1 is a longitudinal section of a first embodiment of the stent according to the invention;

FIG. 2 is a cross-section through said stent in the direction of the arrow II—II in FIG. 1;

FIG. 3 is an end view of the stent in the rolled-up state and fitted around a PTA balloon;

FIG. 4a is a cross-section through an embodiment of the absorbent-material insert;

FIG. 4b is a cross-section through a second embodiment of the absorbent-material insert;

FIG. 5 is a cross-section of an adhesive and marking tape used in the various embodiments according to the invention;

FIG. 6 is a cross-section through a special PTA balloon in the expanded state to be used in combination with the stent according to the invention;

FIG. 10 shows, in a perspective view, the semifinished product obtained by said method;

FIG. 11 shows, partly in a perspective view and partly in cross-section, the stent fabricated from said semifinished product;

DESCRIPTION OF PREFERRED EMBODIMENTS

Figure 7:
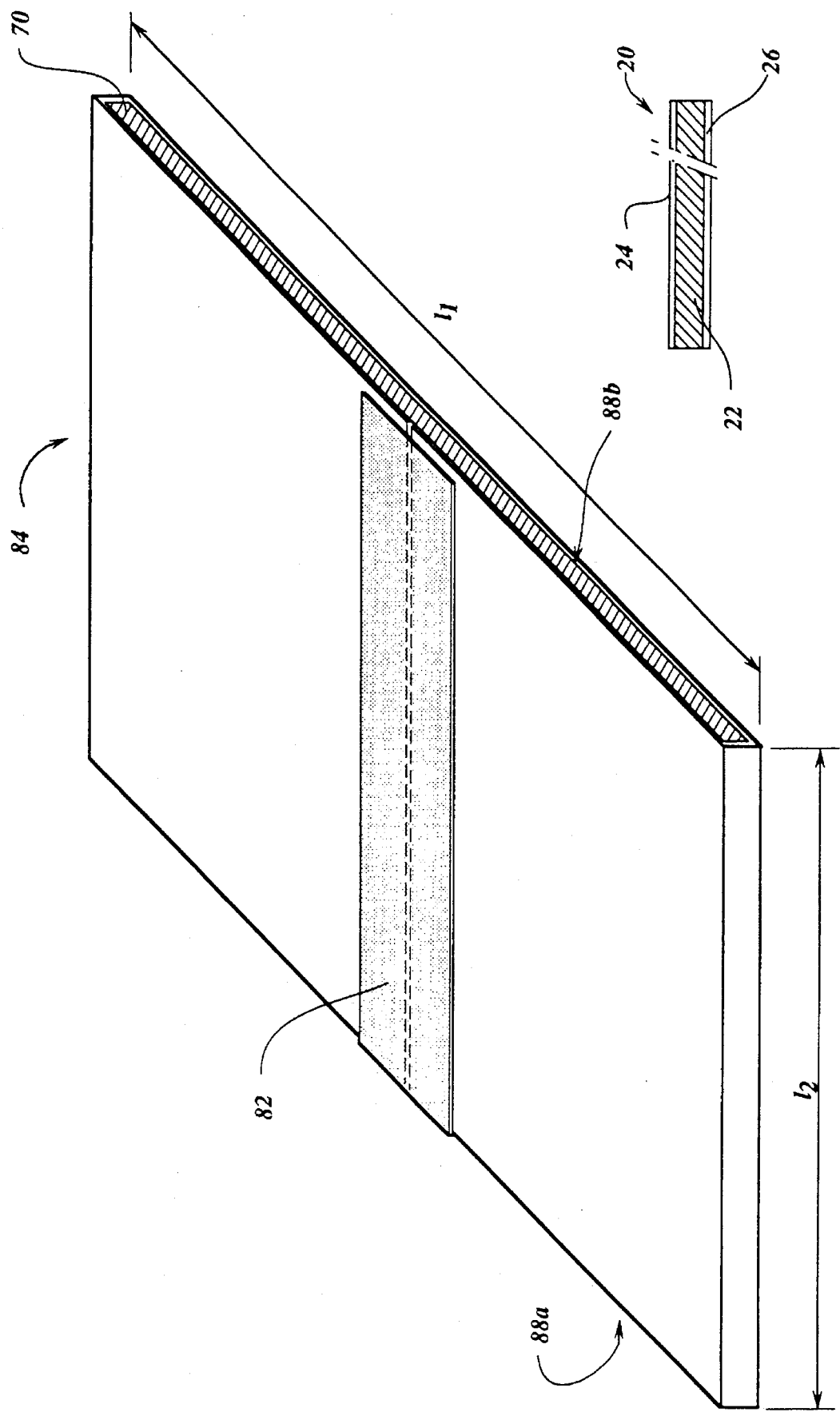
FIG. 7 is a cross-section through another embodiment of such a PTA balloon.
Figure 8:
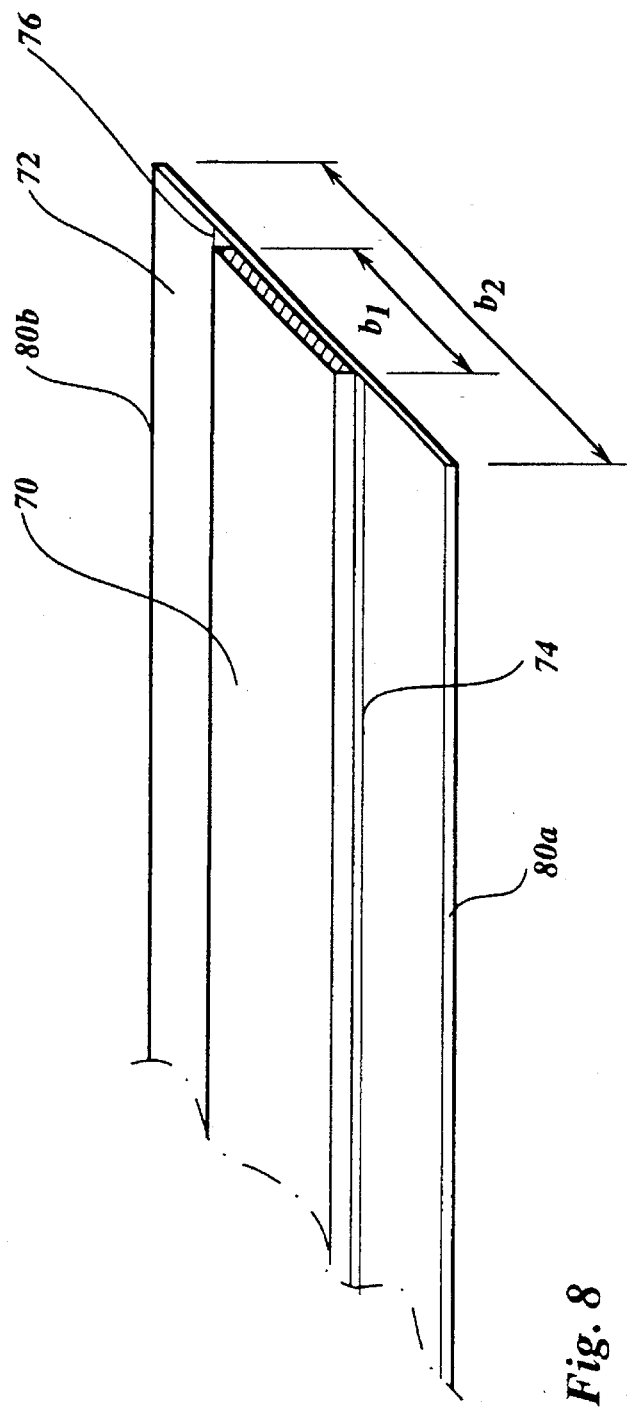
FIGS. 8 and 9 illustrate a preferred method for fabricating the stent according to the invention.
Figure 9:
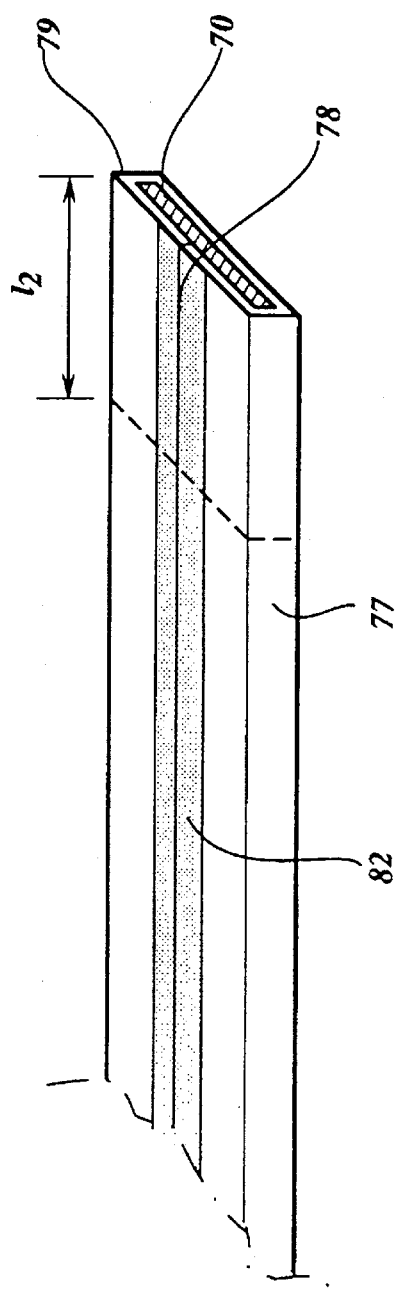

The stent to be discussed below is of the type which is the subject of the intervening Dutch Application 91 01159 and the also intervening European Patent Application 92 201 970.8, both in the name of the Applicant, which are equivalent to EP 0 521 573 and U.S. Ser. No. 07/909,051, filed Jul. 2, 1992, now pending, which is expressly incorporated by reference herein.

The stent 2 shown in FIGS. 1 and 2 comprises an elongated, in this case cylindrical, sleeve 4 which is sealed at both ends and is filled with a curable material, such as an acrylate. This material is of the type which cures when exposed to UV radiation supplied from the outside and consequently fixes the shape which the sleeve-like stent has during the curing. As described in the abovementioned, intervening applications, the stent is brought to the desired position via a body vessel with the aid of a catheter on whose end an inflatable PTA balloon is situated; then the PTA balloon is inflated by injecting into it a suitable high-contrast pressurised fluid, as a result of which the stent, which is spirally wound around it, unfolds and assumes the desired sleeve Shape. FIG. 3 shows diagrammatically the catheter 6, the PTA balloon 8 spirally wound around it and the still unexpanded stent 10 which is also spirally fitted around it. The assembly is held together by biologically degradable thin cords 12 which break during the expansion. A PTA balloon provided with special clamps which secure the rolled-up stent during the introduction and release the stent during the expansion of the balloon may also be used for the introduction.

Such a stent must meet a number of mutually contradictory requirements. The introduction via a body vessel requires that the maximum diameter D1 of the package shown in FIG. 3 must not exceed a value of approximately 7 mm, while the stent must be able to have a diameter D2 of up to 20 mm or even more in the final, expanded state, for example if the stent is designed for the local reinforcement of the wall of the aorta as is necessary in the case of an aneurysm. Certain applications, for example cardiac surgery, require, on the other hand, a diameter of no more than 2.5 mm, while it is very desirable that the final diameter of the stent, that is to say in the expanded state, can be determined accurately beforehand (for example 4.2 mm). Assuming the required dimensions and those of the standard PTA balloon, it follows that, if the sleeve 4 is fabricated from a suitable film material (which according to the invention is not extensible) and which has a minimum thickness of, for example 15 μm which still meets the strength requirements imposed, the distance d between the two mutually opposite walls 4a and 4b may not be more than 0.3 mm. Nevertheless, after the stent has been positioned and expanded, it must have adequate strength and must also be to some extent flexible in the longitudinal direction in order to be able to adapt itself to the body vessel, and the cured synthetic material must be distributed uniformly over the entire space between the walls of the sleeve and in some cases at the same time also permit a certain flexibility.

If the curable material, for example acrylate, is simply provided in the space between the sleeve walls 4a and 4b, these requirements cannot be met. They can, however, actually be met by the stent according to the invention. For this purpose, absorbent material 14 is provided inside the sleeve 4, whose walls are composed of non-extensible material, said absorbent material being impregnated with a curable synthetic material.

Said absorbent material 14 which is impregnated with the curable material ensures not only that the curable synthetic material is uniformly distributed over the entire volume of the sleeve 4, but it contributes appreciably to the strength of the stent obtained in this way after the synthetic material has cured. The absorbent material may be fabricated as a mesh; it may be a nonwoven material and also contain metal threads or filaments.

FIG. 4a shows a cross-section through an embodiment of the absorbent material 14, which, in this case, comprises four layers of mesh-like material 16a–16d laid one on top of the other, each having a thickness of 75 μm, resulting in a total thickness d of 0.3 mm. As a result of this layered structure, the stent retains a certain flexibility even in the final state, with the result that it can easily adapt itself to the shape of the body vessel into which it is introduced.

Even when the sleeve is fitted spirally around the still uninflated PTA balloon–that is to say in the state shown in cross-section in FIG. 3–the absorbent material will ensure that the curable synthetic material is not pressed to one side but remains in position, with the result that, after the unfolding of the sleeve, the synthetic material is uniformly distributed over the entire volume thereof.

Finally, the absorbent material facilitates, as will be explained below, the prefabrication of the stent to no small degree.

FIG. 4b shows an absorbent material 14' which is made up of two mesh-like layers 16e, 16f (obviously, more or fewer layers are also possible) and whose top is covered with a thin film 17 which enhances X-ray contrast, for example a metal layer vapour-deposited thereon. This film fulfills two functions: on the one hand, locating the stent is appreciably facilitated and, on the other hand, this film protects the curable material against undesirable irradiation from the outside during the phase of preparing stent and catheter prior to the introduction thereof.

As shown in FIG. 1, a strip or tape 20 comprising a plurality of layers is preferably provided around the stent at each end, FIG. 5 showing the structure of said strip or tape. Said strip or tape 20 comprises a core 22 having a thin layer 24 of so-called "wound adhesive", a known product, on the outside, that is to say on the side remote from the stent 2. Provided on the other side of the core 22 is a thin layer of adhesive material 26, which bonds the whole to the sleeve wall 4a. The wound adhesive ensures a good adhesion between the expanded stent and the body vessel in which it is fitted, thereby ensuring that the stent remains in position when the catheter is withdrawn along with the PTA balloon. The function of the central strip 21 will be explained in still greater detail below. Obviously, the wound adhesive can also be provided directly on the outer surface of the stent.

The presence of the absorbent material 14 which absorbs and retains the curable material has the consequence that, even if the expanding, radially directed forces are not distributed uniformly over the inner surface during the unfolding of the stent, this does not result in a non-uniform distribution of the curable material; the unfolded stent will nevertheless acquire the desired final shape. This has interesting consequences for the design of the PTA balloon used in the unfolding, as will be explained with reference to FIGS. 6 and 7, which show cross-sections through two different PTA balloons.

FIG. 6 shows a PTA balloon 30 having a stent 32 according to the invention around it, in which absorbent material 38 is provided between the outer wall 34 and the inner wall 36. The PTA balloon 30 is formed from a film material in which permanent groove-like deformations 40 have been formed at regular spacings. The result is that, in the service state, a number of groove-like ducts 44a–44h are present between the PTA balloon 30 and the stent 32 so that, during the fitting of the stent in a blood vessel, the blood flow through said vessel is not completely interrupted. The same effect is achieved with the embodiment shown in FIG. 7. This shows a stent 50 whose space between the outer wall 52 and the inner wall 54 is filled with absorbent material 56; narrow synthetic-material tubes 58a–58h are fastened at a regular spacing on the outer wall 52 of the PTA balloon 53 used in this case and these bring about the same effect as the groove-like ducts 40a–40h in the embodiment shown in FIG. 6.

As has already been stated above, the inventive idea–the retention of the curable synthetic material in absorbent material–appreciably facilitates the fabrication of the stent according to the invention. The method used in connection therewith is explained with reference to FIGS. 8 to 12 inclusive.

The starting point is a strip of absorbent material 70 (which may be layered in the manner shown in FIG. 4 and may be mesh-like material), said strip of absorbent material having a width $b_1$ is laid on a strip of film material 72 having a width $b_2$. The value of $b_2$ is approximately equal to $2 \times b_1$ +twice the thickness of the absorbent material 70. Two folding grooves 74, 76 may be formed at a mutual spacing $b_1$ in the film 72 and the film material 72 is folded around the absorbent material 70 in the manner indicated in FIG. 9, optionally by making use of said folding grooves 74. An adhesive tape 82 is then provided symmetrically with respect to the line 78 over the end edges 80a, 80b, of the film 72, which touch one another. The said tape may have the configuration indicated in FIG. 5. The adhesive layer of the tape, such as the adhesive layer 26, holds the end edges 80a, 80b sealingly together.

Figure 12:
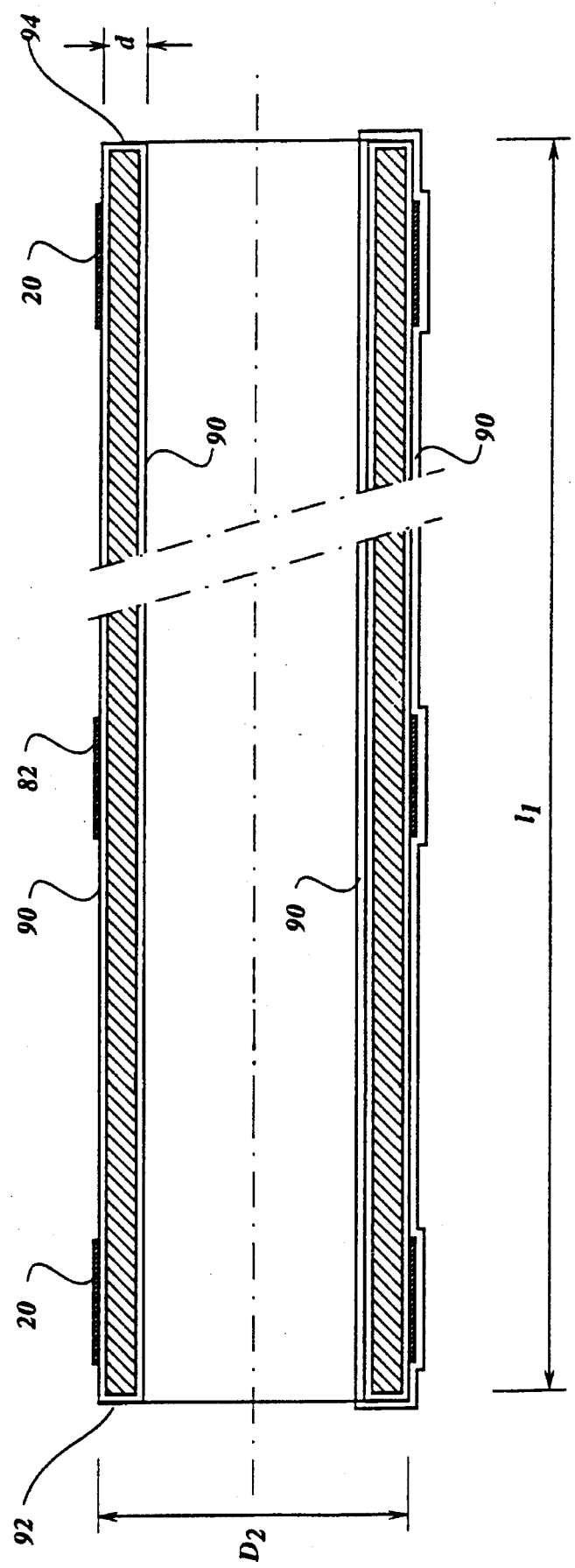
FIG. 12 shows a longitudinal section of said stent and, in particular, along the lines XIIa–XIIa in the uppermost section in FIG. 11 and along the lines XIIb–XIIb in the lowermost section in FIG. 11.

Then a strip having a length $l_2$ is cut from the first semi-finished product obtained in this way, resulting in the second semi-finished product shown in FIG. 10. The dimension $l_1$ of the latter, essentially equal to the width $b_1$ of the mesh material 70 will determine the length of the final stent to be formed therewith, starting from said second semi-finished product, while the dimension $l_2$ determines the diameter in the unfolded state ($D_2 = l_2/\pi$). The procedure is now as follows:

The semi-finished product 84 shown in FIG. 10 is folded around to form the cylinder 86 shown in FIG. 11 over a line parallel to the dimension $l_1$ and, in particular, in a manner such that the end edges 88a, 88b of the second semi-finished product 84 (FIG. 10) lie against one another in the manner shown in FIG. 11. The end edges 88a, 88b are then fixed by means of an adhesive tape 90 extending in the longitudinal direction of the sleeve 88, which results in a sleeve which is closed on all sides, enclosing the mesh material 70 and having a length $l_1$ and a diameter $D_2$ (see also FIG. 12). Said sleeve is closed on all sides because the tape 90 seals the longitudinal seam and its end walls 92, 94 are formed by the folded edges 77, 79 of the film 72 (see FIG. 9). Then the sleeve shown in FIG. 12 is fitted around a PTA balloon in the manner shown in FIG. 3 and fastened. The assembly is then ready for use.

Obviously, many modifications are possible within the scope of the invention. The sleeve may deviate from the circular-cylindrical configuration and may, for example, taper, have a bend and/or have branches. Inner and outer walls may have a mutually different configuration and passage openings, which are in communication with the interior of the sleeve and are situated in its surface, and through which the blood is able to reach the vessel wall locally if the sleeve is used in a blood vessel, may be formed in the sleeve.

The possibility of choosing the curable material, optionally in combination with a single layer of fabric of relatively thick thread, in such a way that it disintegrates if it is subjected to fairly high forces directed radially outwards in the expanded state has already been mentioned; in particular, acrylate is suitable for this purpose.

Figure 13B:
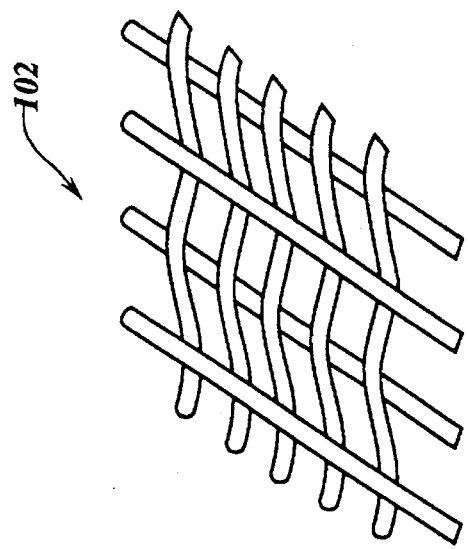
FIGS. 13a–13d show various embodiments of usable absorbent material.
Figure 13D:
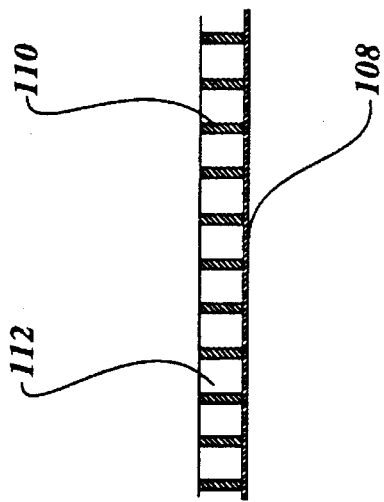
Figure 13A:
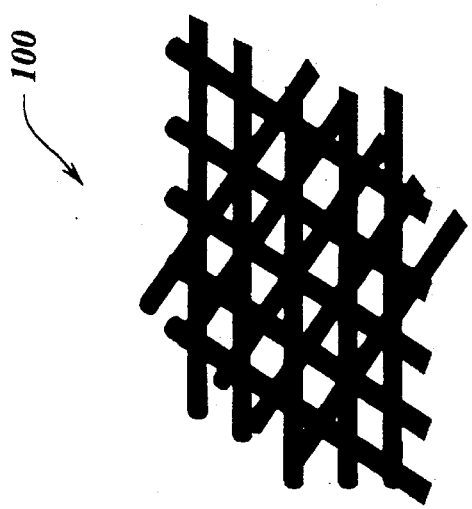
Figure 13C:
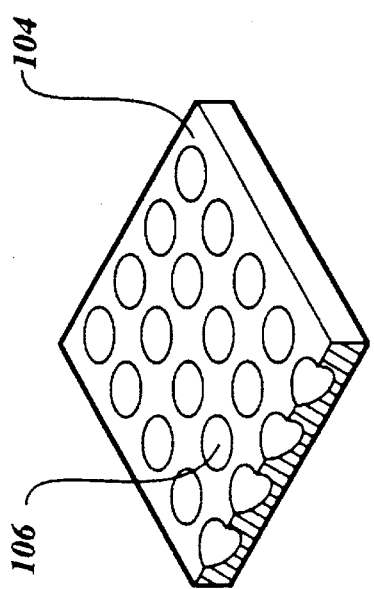

There are also many possibilities as regards the absorbent material. FIG. 13a shows a fairly dense fabric 100 and FIG. 13b shows a more open fabric 102. It is also conceivable to make use of a synthetic-material support 104 having a large number of cavities 106 therein, as shown partly in perspective and partly in section in FIG. 13c. Finally, FIG. 13d shows two films laminated onto one another and, in particular, a very thin support film 108 with a thicker film 110 which is laminated thereon and provided with a large number of absorbing openings 112.

What is claimed is:

1. An expandable double-walled sleeve for locally supporting and reinforcing a body vessel, comprising:

generally tubular inner and outer walls;

absorbent material provided between the inner and outer walls; and curable material contained within the absorbent material.

2. In combination, the sleeve according to claim 1, and a PTA balloon fitted within said sleeve, said balloon having an outer wall provided with ducts preformed in said outer wall for being disposed adjacent to the inner wall of the sleeve, said ducts extending in a longitudinal direction of the balloon and the sleeve.

3. In combination, the sleeve according to claim 1, and a PTA balloon fitted within said sleeve, said balloon having an outer wall provided with tubes secured to said outer wall for being disposed adjacent to the inner wall of the sleeve, said tubes extending in a longitudinal direction of the balloon and the sleeve.

4. Sleeve according to claim 1, wherein said inner and outer walls are made of substantially non-extensible material.

5. Sleeve according to claim 1, in which the absorbent material is composed of a mesh-like material.

6. Sleeve according to claim 5, in which the absorbent material has the form of a fabric.

7. Sleeve according to claim 6, in which the fabric is a single-layer fabric composed of thread.

8. Sleeve according to claim 7, in which the fabric is a nonwoven fabric.

9. Sleeve according to claim 1, in which the absorbent material is provided in a plurality of individual layers.

10. Sleeve according to claim 1, in which the absorbent material contains metal threads.

11. Sleeve according to claim 1, further comprising an identifying mark provided on the sleeve and composed of material which enhances X-ray contrast.

12. Sleeve according to claim 11, in which the contrast-enhancing material is a portion of the absorbent material.

13. Sleeve according to claim 11, in which the contrast-enhancing material is opaque to radiation and covers the absorbent material on the outside of the sleeve.

14. Sleeve according to claim 13, in which the contrast-enhancing material is provided in the form of a strip extending in the circumferential direction of the sleeve.

15. Sleeve according to claim 1, further comprising at least one layer of wound adhesive provided on the sleeve.

* * * * *